(12) United States Patent
Williams

(10) Patent No.: US 9,772,252 B2
(45) Date of Patent: Sep. 26, 2017

(54) LEAKAGE DETECTION IN A MEDICAL DEVICE

(71) Applicant: ETHICON, INC., Somerville, NJ (US)

(72) Inventor: Hal Williams, San Clemente, CA (US)

(73) Assignee: Ethicon, Inc., Somerville, NJ (US)

( * ) Notice: Subject to any disclaimer, the term of this patent is extended or adjusted under 35 U.S.C. 154(b) by 845 days.

(21) Appl. No.: 13/778,274

(22) Filed: Feb. 27, 2013

(65) Prior Publication Data

US 2014/0238110 A1 Aug. 28, 2014

(51) Int. Cl.
| | |
|---|---|
| G01M 3/04 | (2006.01) |
| G01M 3/28 | (2006.01) |
| A61B 1/00 | (2006.01) |
| A61B 90/70 | (2016.01) |
| A61B 1/012 | (2006.01) |
| A61B 90/00 | (2016.01) |

(52) U.S. Cl.
CPC ....... *G01M 3/2846* (2013.01); *A61B 1/00057* (2013.01); *A61B 90/70* (2016.02); *A61B 1/012* (2013.01); *A61B 2090/064* (2016.02); *A61B 2090/0807* (2016.02); *A61B 2090/0809* (2016.02); *A61B 2090/701* (2016.02)

(58) Field of Classification Search
CPC ...................................................... G01M 3/04
USPC .......... 73/40, 49.2, 49.3; 422/28; 604/96.01, 604/99.03, 99.04, 101.01, 21
See application file for complete search history.

(56) References Cited

U.S. PATENT DOCUMENTS

| | | | | |
|---|---|---|---|---|
| 6,513,366 | B1* | 2/2003 | Stauffer | G01M 3/34 |
| | | | | 73/49.3 |
| 6,986,736 | B2* | 1/2006 | Williams et al. | 600/101 |
| 7,340,943 | B2* | 3/2008 | Jackson et al. | 73/49.2 |
| 7,686,761 | B2 | 3/2010 | Jackson et al. | |
| 9,027,389 | B2* | 5/2015 | Abboud | A61B 18/02 |
| | | | | 604/101.01 |
| 2001/0032494 | A1 | 10/2001 | Greszler | |
| 2007/0100203 | A1 | 5/2007 | Jackson et al. | |
| 2007/0185385 | A1* | 8/2007 | Noguchi et al. | 600/132 |
| 2007/0238923 | A1 | 10/2007 | Kubach | |
| 2009/0158539 | A1 | 6/2009 | Onishi et al. | |
| 2011/0058986 | A1* | 3/2011 | Yokoi et al. | 422/111 |
| 2011/0290034 | A1* | 12/2011 | McDonnell et al. | 73/756 |
| 2013/0023920 | A1 | 1/2013 | Terliuc et al. | |
| 2013/0177922 | A1* | 7/2013 | Laugharn et al. | 435/7.1 |

FOREIGN PATENT DOCUMENTS

| | | |
|---|---|---|
| EP | 1769721 B1 | 1/2009 |
| EP | 1433412 B1 | 2/2009 |
| EP | 1433410 B1 | 4/2009 |

* cited by examiner

*Primary Examiner* — Peter Macchiarolo
*Assistant Examiner* — Hoang Nguyen

(57) ABSTRACT

There is provided a method of channel leakage detection in a medical device having one or more channels and a housing having an internal volume surrounding at least a portion of the one or more channels, comprising the steps of (a) pressurizing one or more of the channels by introducing air or gas into the channel; and (b) detecting leakage by monitoring pressure increase in the internal volume of the housing.

4 Claims, 3 Drawing Sheets

LEAKAGE DETECTION IN A MEDICAL DEVICE

FIELD OF THE INVENTION

The present invention generally relates to channel leakage detection in connection with reprocessing or reprocessing systems for medical devices having one or more internal channels that need to be cleaned and/or disinfected after use.

BACKGROUND

Reprocessing and decontamination systems can be used to reprocess previously-used medical devices, such as endoscopes, for example, such that the devices can be used once again. A variety of reprocessing systems exist for reprocessing endoscopes. In general, such systems may include at least one rinsing basin, in which an endoscope that is to be cleaned and/or disinfected can be placed. The basin is commonly supported by a housing that supports a system of lines, pumps, and valves for the purpose of feeding a cleaning and/or disinfecting agent to an endoscope, which has been placed in a rinsing basin. Such devices also include a collection of lines, hoses, conduits, or pipes that are coupled to the pumps and corresponding ports in the endoscope by releasable connectors. Such connectors must achieve a fluid-tight seal while attached to the endoscope, yet be easily releasable at the conclusion of the process.

In various circumstances, an endoscope can include an elongate portion, or insertion tube, having a distal end which can be configured to be inserted into the body of a patient and, in addition, a plurality of channels extending through the elongate portion which can be configured to direct water, air, and/or any other suitable fluid into a patient cavity or site. An endoscope can further include a flexible feed hose or light-conductor casing having inlets and channels that may be in fluid communication with the channels in the elongate portion and, in addition, a control head section having one or more valves, and/or switches, configured to control the flow of fluid through the channels in the flexible feed hose and elongate portion. In various circumstances, an endoscope can include an outer housing, which can include an internal volume, wherein the channels of the flexible feed hose and elongate portion of the endoscope can pass through the internal volume.

During reprocessing, the endoscope is exposed to reprocessing fluids and ingress of reprocessing fluid into the internal volume of the housing from outside the endoscope housing, for example, from the rinsing basin of the reprocessing system, or from ingress of reprocessing fluids into the internal volume of the housing from the channels. Ingress of reprocessing fluids is undesirable since the internal volume of the housing may contain sensitive electronic equipment such as charge coupled device video and ultrasound transducers. Therefore, it is desirable to identify whether the housing and the channels of the endoscope have been compromised prior to exposure to reprocessing fluids that can potentially damage the sensitive electronic equipment residing in the internal volume of the housing, in order to protect the endoscope.

Previous reprocessing systems such as the system described in U.S. Pat. No. 6,986,736, which is incorporated herein by reference in its entirety, test the integrity of the housing to determine whether the housing is compromised by pressurizing the internal volume of the housing directly and monitoring whether pressure drops in the internal volume of the housing over a predetermined time interval. However, this method cannot distinguish if the pressure drop is a result of a leak that is occurring from a breach in a channel that would allow the pressurized fluid to escape from the housing into the channel. The invention disclosed herein provides a method for testing the integrity of the channels of an endoscope to determine whether one or more of the channels are compromised.

SUMMARY

In at least one embodiment, there is provided a method of channel leakage detection in a medical device having one or more channels and a housing having an internal volume surrounding at least a portion of the one or more channels, comprising the steps of (a) pressurizing one or more of the channels by introducing air or a gas into the channel at a sufficiently high flow rate; and (b) detecting leakage by monitoring pressure increase in the internal volume of the housing.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION

Figure 1:
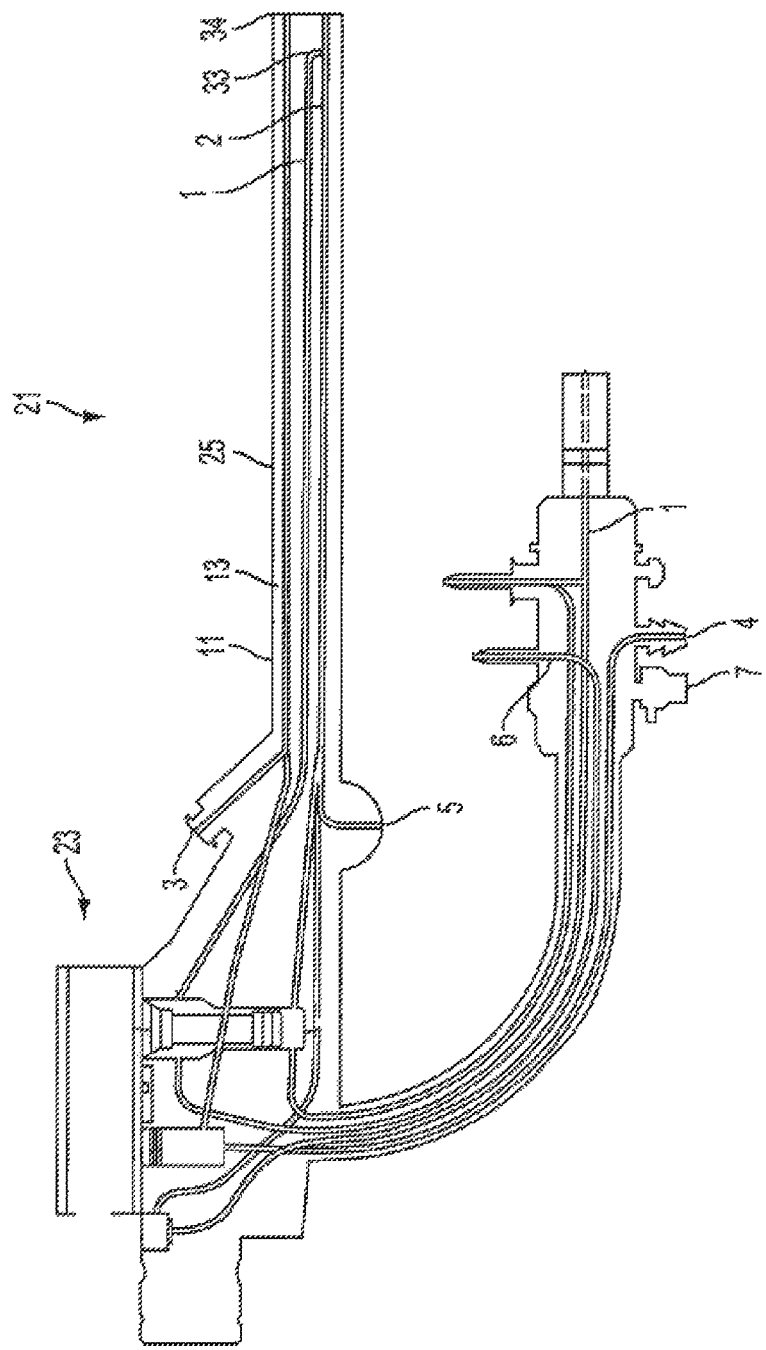
FIG. 1 is an elevational depiction of an endoscope, showing various channels therein.

Referring to FIG. 1, endoscope 21 can include a first channel 1 which may extend, for example, through at least a portion of control head section 23 and elongate portion 25, and to an outlet at distal end 34. Endoscope 21 can also include additional channels 2-6 which can be configured to convey water or a gas or to receive a surgical instrument therein such that the surgical instrument can be guided into the site through the endoscope. In at least one embodiment, flexible feed hose or light-conductor casing can further include leak test connector 7 in fluid communication with an internal volume 13 inside outer housing 11 of the endoscope 21. Leak test connector 7 can be configured to introduce a pressurized fluid and/or vacuum into the internal volume 13 of outer housing 11 in order to inspect the integrity of outer housing 11 for leaks.

After an endoscope has been used, it can be reprocessed such that it can be used once again. In various circumstances, a reprocessing system can be utilized to decontaminate the endoscope and/or evaluate whether the endoscope has been properly decontaminated. In at least one circumstance, water, sterilant, and/or any other reprocessing fluid, can be flushed through one or more of the channels of the endoscope and over the exterior of the housing to remove debris, and/or any other foreign matter, which may have entered into the channels or adhered to the exterior of the endoscope.

Figure 2:
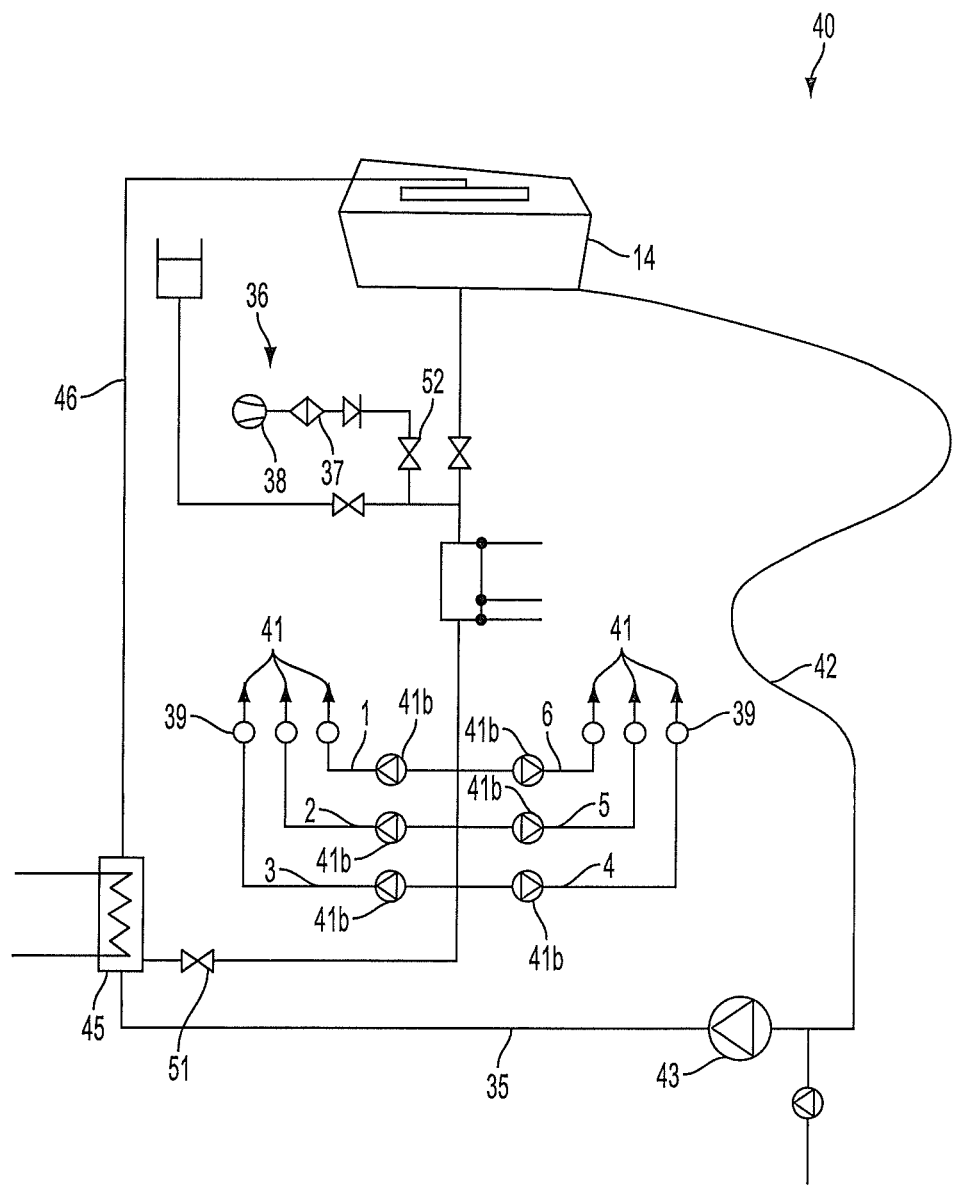
FIGS. 2-3 are schematic representations of at least a portion of a reprocessing system that may be employed in connection with various embodiments of the present invention.

In various embodiments, referring to FIG. 2, reprocessing system 40 can include basin 14 which can be configured to receive at least a portion of an endoscope, for example endoscope 21, therein and, tube 42 which can, in at least one embodiment, be configured to receive at least a portion of, or be in fluid communication with, elongate portion 25 of the endoscope 21. In at least one embodiment, reprocessing system 40 can further include circulation pump 43, which can be configured to circulate fluid from basin 14, for example, through endoscope 21 and/or tube 42, and into line 35. In certain embodiments, pump 43 can also be configured to push the fluid through heater 45 and into line 46 such that the fluid can be circulated back into basin 14, for example. In various embodiments, reprocessing system 40 can further include valve 51 which can be configured to divert at least a portion of the fluid flowing within line 35 through the channels of the endoscope 21. More particularly, in at least one embodiment, reprocessing system 40 can include a number of flush lines 41, which can be configured to receive fluid from line 35, wherein each of the flush lines 41 can be placed in fluid communication with one of the channels of the endoscope 21, i.e., channels 1-6, for example, such that fluid, air, gas, etc. can flow therethrough. Each flush line 41 may be connected to an outlet of a channel pump 41b. The pumps 41b are preferably peristaltic pumps or the like that, for example, pump fluid, such as liquid and air, through the flush lines 41 and any internal channels of the endoscope 21. The channel pumps 41b either can draw liquid flowing within line 35 through valve 51, or can draw decontaminated air from an air supply system 36 through a valve 52. The air supply system 36 can include a pump 38 and a microbe removal air filter 37 that filters microbes from an incoming air stream. In various embodiments, each flush line 41 may be provided with a dedicated channel pump 41b to ensure adequate fluid pressure and to facilitate the individual monitoring of the fluid pressure in each flush line 41. In at least one such embodiment, a sensor, such as sensor 39, for example, can be in fluid communication with each flush line 41 for sensing excessive pressure in the flush line 41.

To perform the channel leakage detection test of the present invention on, for example, channel 1 of the endoscope 21, system 40 may be configured to monitor fluid communication between channel 1, and the internal volume 13 of outer housing 11. Detection of fluid communication can be indicative of fluid leakage from channel 1 into the internal volume 13 of outer housing 11, which can indicate that channel 1 may be compromised. To monitor fluid communication between channel 1 and internal volume 13 of outer housing 11, in one embodiment, system 40 may be configured to pressurize channel 1 by flowing air or any suitable gas, and monitor a change in pressure in the internal volume 13 of outer housing 11.

In certain embodiments, referring to FIG. 2, to perform the channel leakage detection test on channel 1, a flush line 41 may be coupled to channel 1 as described above. A microcontroller may cause valve 52 to open in order to allow for fluid communication between air pump 38 and the flush line 41. The microcontroller may then cause air pump 38 to be activated. Air may flow from air pump 38 through valve 52. As described above, each flush line 41 may include a separate pump 41b and a separate sensor 39 to accurately control and monitor pressure within each channel. In some embodiments, pump 41b can be a peristaltic pump or the like that pumps fluid, such as liquid and air. In this event, the microcontroller may cause the pump 41b associated with channel 1 to be activated in order to pressurize channel 1 to about 2 to 30 psig, and even as low as about 3 to 5 psig. As pressure is maintained in channel 1, the microcontroller may obtain several readings from a pressure sensor which measures pressure in the internal volume 13 of outer housing 11. An increase in pressure of the internal volume 13 of outer housing 11, beyond a predetermined baseline value, such as an increase of about 0.05 to 0.5 psig, preferably about 0.1 to 0.3, or about 0.2 psig or more within a period of 1 minute or longer if the channels are pressurized to lower pressures, may prompt the microcontroller to stop the test and report a failure in the integrity of channel 1. If no change, or a change below the predetermined baseline value, is detected, the microcontroller may report a successful completion of the channel leak detection test by channel 1. The channel leak detection test may be repeated for each of the channels of endoscope 21. An increase in the pressure of internal volume 13 as a result of pressurizing channel 1 can indicate fluid communication between channel 1 and outer housing 11, which can indicate a compromise in channel 1.

As outlined above, reprocessing system 40 may sequentially test each of the channels 1-6 of endoscope 21 and determine separately whether each of the channels 1-6 is compromised. In an alternative embodiment, reprocessing system 40 may test all or some of the channels 1-6 simultaneously. For example, all of the channels 1-6 of the endoscope 21 can be pressurized simultaneously and the internal volume 13 of outer housing 11 can be monitored for a change in pressure, as described above. If no change, or a change below the predetermined baseline value, is detected, reprocessing system 40 may report a successful completion of the channel leak detection test by channel 1-6. If a change in pressure, beyond the predetermined baseline value, is detected, reprocessing system 40 may report that at least one of the channels 1-6 of endoscope 21 is compromised.

In various embodiments, the channel leakage detection test, outlined above, can be performed before, during, and/or after reprocessing of endoscope 21. Performing the channel leakage detection test, for example, prior to the introduction of reprocessing fluids, such as decontamination liquids, into the channels 1-6 of endoscope 21, may mitigate the possibility of contaminating the internal volume 13 of outer housing 11 with reprocessing fluids during the reprocessing procedure.

Figure 3:
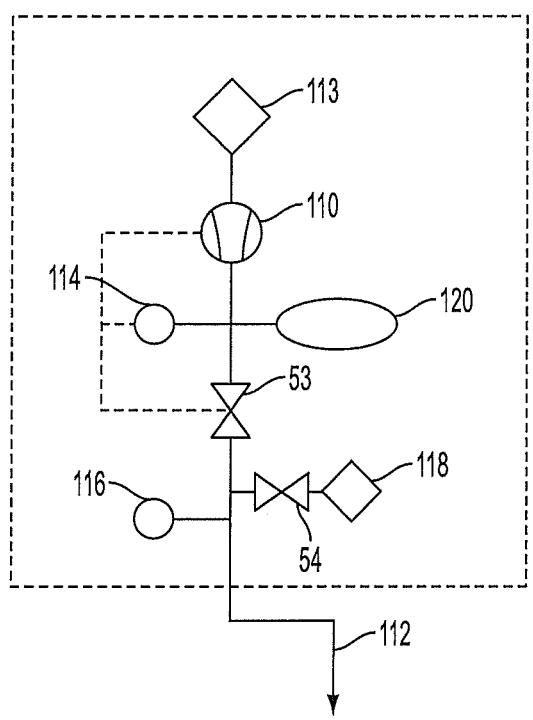

Referring to FIGS. 1 and 3, the integrity of outer housing 11 is preferably tested according to the method described in U.S. Pat. No. 6,986,736 before the channel leakage detection test of the present invention, wherein conduit 112 can be coupled to leak test connector 7 of outer housing 11 to allow fluid communication between air pump 110 and the internal volume 13 of outer housing 11 when valve 53 is in the open position. While air is a suitable pressurization medium, other gases could be used. To begin the test, valve 53 may be turned into an open position, and air pump 110 can be activated to pump air through conduit 112 and into outer housing 11 to pressurize the internal volume 13 of outer housing 11, which may initially be at ambient pressure. Upon reaching a desired pressure, for example about 2 to 5 psig, the valve 53 may be closed, and air pump 110 deactivated. A pressure sensor 116 may look for a change in pressure in the internal volume 13 of outer housing 11, which could indicate a compromise in the integrity of outer housing 11. In at least one embodiment, pressure sensor 116 may look for a decrease in pressure in internal volume 13 of outer housing 11. A decrease in pressure, beyond a predetermined acceptable range, for example a decrease in pressure of about 0.05 to 0.5, preferably about 0.1 to 0.3 psig within a period of 1 minute, may indicate the escape of air through outer housing 11, which may indicate a compromise in the integrity of outer housing 11. Alternatively, instead of pressurizing the internal volume of the outer housing, a vacuum may be created in the internal volume, and the pressure sensor could look for an increase in pressure in the internal volume of the outer housing, which may indicate a compromise in the integrity of the outer housing. A control system which may have a microcontroller may be configured to be in communication with air pump 110, valve 53 and pressure sensor 116 to manage the testing of outer housing 11 as outlined above. If outer housing 11 of endoscope 21 fails the test, the control system may report a test failure. Alternatively, if outer housing 11 of endoscope 21 passes the test, the microcontroller may cause valve 54 to open in order to vent the conduit 112 and return outer housing 11 to ambient pressure prior to conducting the channel leakage detection test of the present invention.

Referring again to FIG. 3, system 40 may include a valve 54, which may selectively vent the conduit 112, and the housing 11 through an optional filter 118 when the testing procedure is complete. System 40 may also include an air buffer 120 to smooth out pulsation of pressure from the air pump 110. A HEPA or other microbe-removing filter 113 may remove microbes from the pressurizing air; and an overpressure switch or relief valve 114 may prevent accidental over pressurization of outer housing 11 of endoscope 21 during testing.

The embodiments described herein are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A method for reprocessing an endoscope having an elongate portion, a plurality of channels extending through the elongate portion, and a housing having an internal volume, wherein the plurality of channels pass through the internal volume, comprising the steps of:
   (a) pressurizing the internal volume of the housing by introducing air or a gas into the internal housing;
   (b) detecting leakage by monitoring pressure decrease in the internal volume of the housing;
   (c) venting the internal volume of the housing;
   (d) pressurizing one or more of the channels by introducing air or a gas into the channel; and
   (e) detecting leakage by monitoring pressure increase in the internal volume of the housing.

2. The method of claim 1, wherein an indication is provided if a pressure decrease in step (b) or an increase in pressure in step (e) is detected, each of which exceeds predetermined baseline values.

3. The method of claim 2, wherein the internal volume of the housing is pressurized to about 2 to 5 psig in step (a), and the one or more channels is pressurized to about 2 to 30 psig in step (d), and the indication is provided if the pressure decrease in step (b) exceeds 0.05 to 0.3 psig within 1 minute or the increase in pressure in step (e) exceeds 0.05 to 0.3 psig within 1 minute.

4. A method for reprocessing an endoscope having an elongate portion, a plurality of channels extending through the elongate portion, and a housing having an internal volume, wherein the plurality of channels pass through the internal volume, comprising the steps of:
   (a) creating a vacuum in the internal volume of the housing;
   (b) detecting leakage by monitoring pressure increase in the internal volume of the housing;
   (c) venting the internal volume of the housing;
   (d) pressurizing one or more of the channels by introducing air or a gas into the channel; and
   (e) detecting leakage by monitoring pressure increase in the internal volume of the housing.

* * * * *